United States Patent [19]

Prost

[11] 4,437,470
[45] Mar. 20, 1984

[54] PROCESS AND APPARATUS FOR MEASURING BLOOD PRESSURE

[75] Inventor: Jean-Louis Prost, Geneva, Switzerland

[73] Assignee: Battelle Memorial Institute, Carouge, Switzerland

[21] Appl. No.: 378,254

[22] Filed: May 14, 1982

Related U.S. Application Data

[63] Continuation-in-part of Ser. No. 181,620, Aug. 26, 1980, abandoned.

[30] Foreign Application Priority Data

Aug. 28, 1979 [CH] Switzerland .................. 7785/79

[51] Int. Cl.³ ............................................... A61B 5/02
[52] U.S. Cl. .................................. 128/679; 128/667
[58] Field of Search ........................... 128/666–667, 128/679, 687–690

[56] References Cited

U.S. PATENT DOCUMENTS

| | | | |
|---|---|---|---|
| 3,192,921 | 7/1965 | Erickson et al. | 128/667 |
| 3,229,685 | 1/1966 | Ringkomp et al. | 128/667 |
| 3,482,565 | 12/1969 | Gowen | 128/667 |

OTHER PUBLICATIONS

Hommer, W. E. et al., "Indirect BP Finger Cuff", IBM Tech. Discl. Bulletin, v 8, #4, Sep. 1965.

*Primary Examiner*—Kyle L. Howell
*Assistant Examiner*—Francis J. Jaworski
*Attorney, Agent, or Firm*—Karl F. Ross

[57] ABSTRACT

A photoelectric transparency detector juxtaposed under a certain contact pressure with the tip of a finger works into a computer also receiving the values of an astringent pressure simultaneously applied to another part of the finger by an inflatable air cushion of a flow-blocking cuff. The computer calculates a predetermined fraction, specifically one-half, of the sum of several air-pressure values measured during a period of progressive relaxation of the astringent pressure, taken at instants coinciding with certain points of a continuous curve representing changes in the mean transparency of a skin area contacted by the detector, which constitutes a close approximation of systolic blood pressure. Diastolic blood pressure may be measured during a heartbeat immediately following a low point of the mean-transparency curve.

10 Claims, 3 Drawing Figures

PROCESS AND APPARATUS FOR MEASURING BLOOD PRESSURE

CROSS-REFERENCE TO RELATED APPLICATION

This is a continuation-in-part of my copending application Ser. No. 181,620 filed Aug. 26, 1980 and abandoned concurrently with the filing of the present application.

FIELD OF THE INVENTION

My present invention relates to the measurement of blood pressure.

BACKGROUND OF THE INVENTION

The method of measuring blood pressure that is most universally known consists in compressing the arm of a person with an inflatable cushion until the blood is interrupted, after which the pressure is progressively decreased and the re-establishment of the blood circulation is detected acoustically by means of the "Korotkoff noises" which are produced when the pressure decreases from the systolic pressure to the diastolic pressure. The "Korotkoff noises" are detected by means of a stethoscope place between the inflatable cushion and the skin.

There has already been proposed an automation of this process for wider public use by incorporating a microphone into the inflatable cushion and by connecting it to an electronic circuit for automatically determining the systolic and diastolic pressures. A drawback of such arrangements arises mainly from the fact that it is not easy to wrap by oneself an inflatable cushion around the arm and that it is necessary to remove any clothing covering the arm. Although such constraints may be unimportant within the frame of the medical profession, they constitute an impediment to wide public utilization, especially when the pressure measurement is to be made on a person's own body.

French Pat. No. 1,334,572 describes an apparatus for measuring blood pressure by the detection of light-absorption variations through a portion of the ear lobe subjected to a variable pressure. Thus, the application of such pressure drives the blood of this portion from the ear lobe and the detecting device will measure the volume of remaining blood. The measured value, of course, varies with the same frequency as the heartbeat. For drawing a curve of the transparency variations, it is necessary to measure the maximum values and to calculate the curve from these values, after which the systolic and diastolic pressures are deduced from some specific values of this curve on the basis of particular relations existing between these values and the systolic and diastolic pressures.

The calculation of the curve of pressure variations requires the use of a relatively complex electronic circuit which results in a rather expensive system not suitable for making an apparatus intended for wide public use. Moverover, the transparency measurement which is contemplated in the French patent can only be made on the ear lobe which is not an ideal measuring spot for an apparatus designed for use by the general public and not reserved exclusively to doctors.

French Pat. No. 2,052,617 and U.S. Pat. No. 3,412,729 concern oxymeters from which the blood pressure can be obtained indirectly. This measurement is based on the absorption of infrared light by tissues which varies in inverse proportion to the amount of blood, the latter varying in turn according to the blood pressure. The signal given by this measurement is alternating which makes the determination of the diastolic and systolic pressures relatively difficult to perform. Such devices are generally intended for hospitals and are not suited for being sold outside the specialists' field U.S. Pat. No. 3,698,382 concerns a device for driving the blood from the area underneath a portion of skin by pressure application and for measuring the blood-return rate in such area which is a function of the blood pressure. Such a device is, however, not adapted for measuring systolic and diastolic pressures.

It has already been proposed to measure the blood pressure from a finger. In such a case, the blood stream can be detected optically by means of a photoplethysmograph which measures the light transmission through the skin varying in accordance with the heartbeat. Consequently, when the blood circulation is stopped, the signal from the photoplethysmograph is essentially constant; it becomes again variable when the circulation is re-established.

This process enables a general measurement of the systolic pressure, with extremely questionable reliability. A measurement of diastolic pressure by this process has no practical significance since large variations occur from one measurement to the next.

The difficulties result from several factors, including the pressure difference between the arm and the fingers where the arteries have a much smaller diameter. Even if the pressure is measured correctly, the result will be different from the value obtained on the arm which constitutes a unviersal standard. Moveover, the pressure measured in this manner can vary under the influence of other factors so that it is difficult to set up comparisons between several measurements on the same person, owning to the vaso-constrictive automatic control of the quantity of blood that circulates in the extremities (hands and feet) as a function of the energy requirements of other parts of the body. Thus, the amount of blood in the fingers is smaller during digestion or when the weather is cold, which is an additional factor that may alter the pressure difference between the arm and the fingers and may also cause discrepancies between two measurements done on a finger when the intervening time is significant. Thus, not only is the finger measurement not comparable to the arm measurement, but two successive finger measurements done under different conditions are frequently divergent.

OBJECT OF THE INVENTION

My invention, therefore, aims at providing a method of and means for remedying, at least in part, the abovementioned drawbacks.

SUMMARY OF THE INVENTION

In accordance with my present invention, the flow of blood is detected optically by means of a photoelectric sensor that measures the transparency of a skin area situated downstream of an anatomical part on which the blood circulation has been stopped by the application of external astringent pressure. This process comprises the steps of applying the photosensitive element to that area with a contact pressure ranging between 50 and 150 g/cm$^2$, plotting a continuous curve of the average transparency as a function of time, and measuring a certain number of pressure values at three or four instants corresponding to characteristic points of the transparency curve while the applied astringent pressure is progressively decreased. I have found that a predetermined fraction of the sum of these pressure values will give a good approximation of the systolic blood pressure; more particularly, half the sum of three values respectively corresponding to an upper inflection point, a low point and a leveling-off point of the mean-transparency curve will give optimum results. A fourth value, measured at an instant which coincides with a heartbeat immediately following the aforementioned low point, is representative of diastolic blood pressure.

My improved process enables the direct and continuous measurement of the blood pressure at a location different from that where the external pressure is exerted; the photoelectric sensor is applied to the measuring area with a contact pressure sufficiently weak so as not to interfere with the astringent pressure exerted upstream of this measuring area. This enables a considerable simplification of the electronic circuit for processing the measured signals.

In the preferred embodiment described hereinafter, the measuring area is the tip of a person's finger and the astringent pressure is applied to that finger ahead of its first joint.

BRIEF DESCRIPTION OF THE DRAWING

The above and other features of my invention will now be described in detail with reference to the accompanying drawing in which.

SPECIFIC DESCRIPTION

Figure 1:
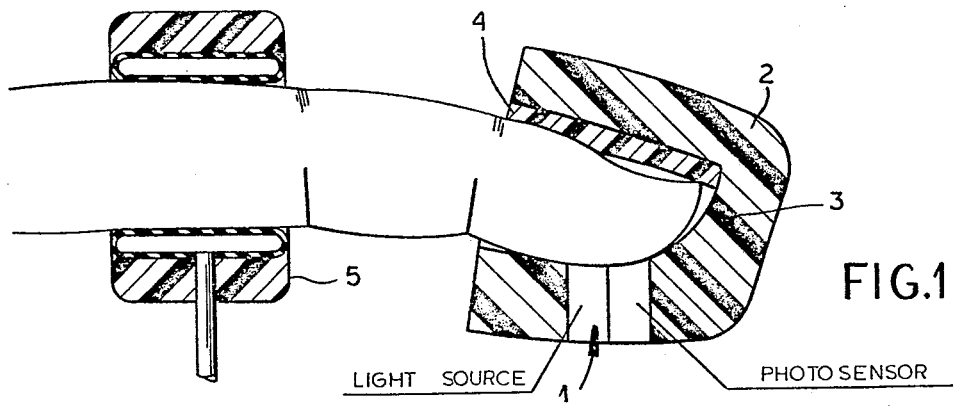
FIG. 1 is a schematic view of a measuring element used in blood-pressure measurements according to my invention.

As briefly discussed above, the photoelectric sensing of the transparency of superficial tissues enables the detection of an alternating signal whose frequency corresponds to that of the heartbeat rhythm. This measuring can be done with a photoplethysmograph which comprises a cell 1 with a transparent contact surface, the cell being divided into two parts by a partition. One of the parts carries a light source, e.g. an infrared lamp, while the other contains a photoelectric detector. A cell of this character, serving for the detection of objects by reflection, is commercially available under the mark "OPTRON", Type OPB-730. The cell is enclosed in a cap 2 having a recess 3 fitting around the tip of the finger of a patient whose blood pressure is to be tested. This cap is provided inside with a pad 4 of resiliently compressible material such as foam plastic for ensuring proper contact of the cell with the finger and accommodates, to a certain extent, variations of finger size. A cuff 5 with an air cushion 17 for blocking the arterial blood flow is placed around the same finger ahead of its first joint and thus upstream of cap 2.

Figure 3:
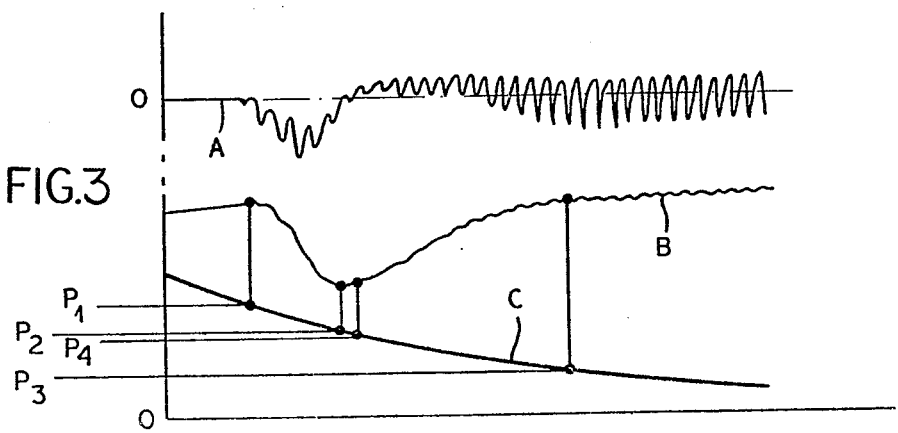
FIG. 3 is a set of graphs pertaining to this process.

Systematic transparency measurements, carried out downstream of a portion of a finger in which blood flow has been stopped by such a cuff, have shown that, when the blood circulation is restored, a mean-transparency curve B represented in FIG. 3 drops suddenly to reach a minimum value after which it progressively rises again to finally get stabilized at a practically constant level. It should be noted that this curve, which is the same for any individual, can be plotted only if the contact pressure between the photoplethysmograph and the skin lies between well-defined limits ranging from about 50 g/cm$^2$ to 150 g/cm$^2$. My experiments were performed with a pressure of about 100 g/cm$^2$. I have found, indeed, that if the pressure is too low or too high one still obtains an alternating electrical signal as a function of the cardiac rhythm, represented by a curve A in FIG. 3, but not the mean-transparency curve B. Now, the usefulness of this curve B resides in the fact that it is a characteristic of the blood circulation following the release of the astringent pressure of the flow-blocking cuff. Moreover, this curve B has some inflection points which constitute markers that are particularly well suited for electronic processing. It is, however, not possible to establish a direct relationship between this curve B and the "Korotkoff noises". Thus, this curve does not yield directly the systolic and diastolic pressures, especially if one desires that such pressures be comparable to the corresponding pressures measured on the arm and be relatively independent of the physiological conditions under which the measurements are undertaken.

Consequently, the measured pressures must be processed for enabling an evaluation of the systolic and diastolic pressures.

This treatment involves a standardization of the process and of the equipment for carrying it out. For achieving such standardization, there were undertaken a series of measurements on a sample group of persons, systematically correlating the mesurements on the arm with those on the finger. By this means I was able to statistically establish a correlation between the pressures measured on the arm, considered as reference pressures, and those read at various significant points of curve B. I have found that there are three characteristic pressure values $P_1$, $P_2$ and $P_3$ correlated with as many significant points. Value $P_1$ corresponds to the characteristic pressure at a first, upper inflection point of curve B, i.e. a point of incipient descent which coincides with beginning restoration of the blood circulation and theoretically corresponds to the systolic pressure in the finger but is poorly reproducible for the reasons previously explained and can differ significantly from the reference pressure. Value $P_2$ corresponds to the characteristic pressure at a low point of curve B whereas value $P_3$ corresponds to the characteristic pressure at a location where the curve levels off after rising from that low point and becomes substantially flat, albeit with a slight ripple as shown. These pressures are measured by correlating the curve B with a curve C that corresponds to the progressively decreasing astringent pressure applied to the air cushion 17 of cuff 5.

A good approximation of the conventionally determined systolic reference pressure, on the average with ±5%, is achieved by a mathematical evaluation of the measured values according to the following equation:

$$P_s \simeq (P_1 + P_2 + P_3)/2$$

This calibration corresponds to an approximation based on the aforementioned sample group of persons and is statistically valid for a larger population. However, such calibration does not take into account some individuals with pathological disorders of the blood stream. Although a possibility of individual calibration does exist, it should be borne in mind that the process and apparatus according to my invention are not intended to replace the existing sphygmomanometers used by medical practitioners but offer a simple means enabling anyone to measure his or her own blood pressure and giving a result comparable to the pressure measured on the arm.

By the same statistical measurements I have been able to define a calibration serving to evaluate the diastolic pressure with the aid of the present apparatus in a manner comparable to the pressure measured on the arm. The pulsating curve A of FIG. 3 corresponds to a high-frequency component of the variation of the transparency of the finger whose average level is given by curve B, these pulsations occurring in the rhythm of the heartbeat. A statistically good approximation of the reference diastolic pressure can be obtained by measuring a pressure $P_4$ at an instant following by one heartbeat the low point of curve B coinciding with pressure $P_2$. Hence, it is sufficient to identify on curve A the beat that follows the lower inflection point of curve B and to check at this moment the pressure value $P_4$ on curve C to obtain an approximation of the diastolic reference pressure.

Figure 2:
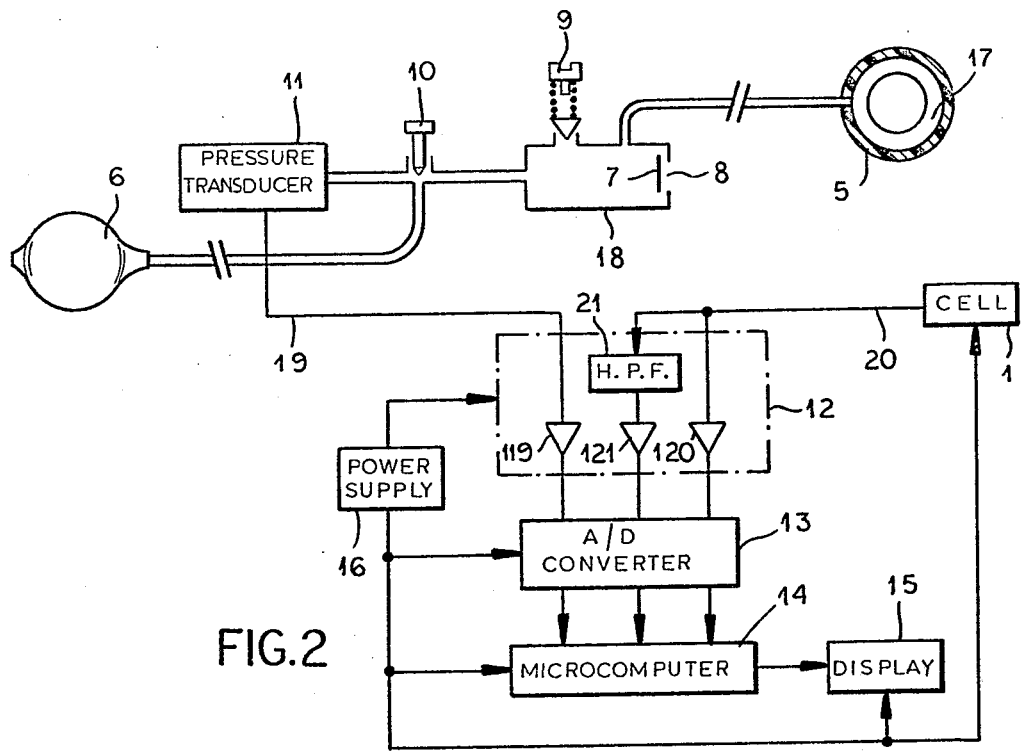
FIG. 2 is a block diagram of an apparatus for carrying out the present process.

The apparatus shown in FIG. 2 includes the cuff 5 whose inflatable cushion 17 is connected to a pressure source comprising a ball-shaped pumping element 6 and a check valve 7 overlying an air inlet 8 of a plenum chamber 18. A spring-loaded safety valve 9 enables air to escape from that chamber when the pressure therein exceeds a given limit. A manually controlled venting valve 10 serves for progressively reducing the pressure in the cuff 5 to restore the blood flow. This air-pressure generator is connected to a pressure transducer 11 whose output is connected to a signal-processing circuit 12.

The air pressure prevailing in plenum chamber 18, corresponding to the astringent pressure exerted upon the patient's finger by cushion 17, is converted by transducer 11 into a first electrical signal appearing on an input lead 19 of processing ciruit 12; this signal is fed to an amplifier 119. Another input lead 20 of circuit 12, originating at cell 1, carries a second electrical signal emitted by its photosensor whose time constant is so chosen that the high-frequency fluctuations of the returning blood circulation are almost totally suppressed in the mean-transparency curve B which is representative of that signal as it appears in the output of an amplifier 120. The signal on lead 20 is also delivered to an amplifier 121 via a circuit branch in parallel with amplifier 120, that branch including a high-pass filter 21 which suppresses the d-c component of the signal and emphasizes its alternating component at the frequency of the heartbeat; the result is the curve A of FIG. 3 which, it should be noted, has a zero level different from that of curves B and C. Filter 21 may also be regarded as a differentiator deriving the curve A from the residual ripples of curve B. It is, of course, also possible to operate with a smaller time constant of the photosensor and to insert a low-pass filter or integrator in series with amplifier 120.

The outputs of amplifiers 119, 120 and 121 are connected to an analog/digital converter 13 working into a microcomputer 14 which calculates the systolic pressure $P_s$ from values $P_1$, $P_2$, $P_3$ according to the foregoing equation and also determines the diastolic pressure from the value of curve C appearing with a delay of one cycle of curve A after the low point of curve B corresponding to pressure $P_2$. The calculated systolic and diastolic pressures appear on the screen of a display device 15 connected to microcomputer 14. A power supply 16 energizes the elements of circuit 12, the converter 13, the microcomputer 14 and the display 15 as well as the constituents of cell 1.

While the formula for the systolic pressure $P_s$ based on the measured values $P_1$, $P_2$ and $P_3$ is strictly empirical, its accuracy has been confirmed by the aforementioned tests carried out at different times with several tens of persons. Each test was preceded by conventional measurements of the reference pressure on the arm of the subject. The tests showed that the calculated pressure $P_s$ approximates more closely the reference value than does the pressure $P_1$ measured at the instant of beginning restoration of blood circulation. The value $P_s$ has also proven more readily reproducible than the value $P_1$, being less dependent on physiological factors tending to vitiate the result. The value $P_4$ found in each instance for the calculated diastolic pressure also corresponded rather closely to that measured conventionally; this can be considered a significant improvement over prior attempts to determine the diastolic pressure by observing the optical equivalent of the disappearance of the "Korotkoff noises".

The disclosed apparatus is simple, easy to operate, and practical as a means enabling the general public to carry out blood-pressure measurements compatible with those obtainable with the sphygmomanometers commonly used in the medical profession.

I claim:

1. A process for measuring a person's blood pressure, comprising the steps of:
    (a) temporarily blocking the flow of blood on an extremity of such person's body by the application of astringent pressure;
    (b) applying a photosensitive element to an illuminated skin area of said extremity, downstream of the flow-blocking location, with a contact pressure ranging between substantially 50 and 150 g/cm$^2$;
    (c) continuously measuring an output signal of said photosensitive element, representative of the instantaneous transparency of said skin area, during a period of progressive relaxation of said astringent pressure;
    (d) averaging said output signal to obtain a mean-transparency curve plotted against time;
    (e) measuring several values of said astringent pressure at instants corresponding to respective points of said mean-transparency curve; and
    (f) calculating a predetermined fraction of the sum of said several values as an indication of systolic blood pressure.

2. A process as defined in claim 1 wherein the values measured in step (e) are a first value taken at an instant corresponding to an upper inflection point of said curve, a second value taken at an instant corresponding to a low point of said curve, and a third value taken at an instant corresponding to a leveling-off point of said curve.

3. A process as defined in claim 2 wherein said fraction is calculated in step (f) as one-half the sum of said first, second and third values.

4. A process as defined in claim 2 or 3, comprising the further step of measuring an additional value of said astringent pressure at an instant coinciding with a heartbeat immediately following said low point of said curve as an indication of diastolic blood pressure.

5. A process as defined in claim 1, 2 or 3 wherein steps (a) and (b) are performed on the person's finger.

6. An apparatus for measuring a person's blood pressure, comprising:
- a cuff provided with an air-inflatable cushion applicable to an extremity of a person's body for exerting an astringent pressure temporarily cutting off the blood flow;
- a detector including a light source and a photosensor positionable, with a contact pressure ranging between substantially 50 and 150 g/cm$^2$, on a skin area of said extremity downstream of said cuff;
- operating means connected with said cushion for inflating and controlledly deflating same;
- transducer means coupled with said operating means for converting measured values of said astringent pressure into first electrical signals representative of blood pressure;
- circuit means connected to said detector for continuously converting output signals of said photosensor into second electrical signals representative of the mean transparency of said skin area; and
- computer means connected to said circuit means and to said transducer means for calculating a predetermined fraction of the sum of several values of said first electrical signals, coinciding with predetermined points of a mean-transparency curve derived from said second electrical signals, as an indication of systolic blood pressure.

7. An apparatus as defined in claim 6, further comprising display means connected to an output of said computer means.

8. An apparatus as defined in claim 6 or 7 wherein said circuit means includes a differentiator deriving from said curve a high-frequency component representative of the person's heartbeat rhythm for enabling the calculation by said computer means of a further value of said first electrical signals, following by one heartbeat a low point of said curve, as an indication of diastolic blood pressure.

9. An apparatus as defined in claim 8 wherein said differentiator comprises a high-pass filter.

10. An apparatus as defined in claim 6 or 7 wherein said cuff fits around a person's finger, said detector comprising a cap accommodating a fingertip.

* * * * *